(12) United States Patent
Aboujaoude (10) Patent No.: US 8,302,228 B2
(45) Date of Patent: Nov. 6, 2012

(54) LOWER EXTREMITY SURGICAL POSITIONING DEVICE

(76) Inventor: Emad Aboujaoude, Portland, OR (US)

( * ) Notice: Subject to any disclaimer, the term of this patent is extended or adjusted under 35 U.S.C. 154(b) by 337 days.

(21) Appl. No.: 12/711,251

(22) Filed: Feb. 23, 2010

(65) Prior Publication Data

US 2010/0263129 A1    Oct. 21, 2010

Related U.S. Application Data

(60) Provisional application No. 61/154,773, filed on Feb. 24, 2009.

(51) Int. Cl.
*A61G 13/12* (2006.01)
*A61G 7/075* (2006.01)
(52) U.S. Cl. ............ 5/648; 5/651; 5/624; 128/882
(58) Field of Classification Search ............ 5/602, 624, 5/648–651; 128/882
See application file for complete search history.

(56) References Cited

U.S. PATENT DOCUMENTS

| | | | | |
|---|---|---|---|---|
| 2,067,891 A | * | 1/1937 | Comper | 5/624 |
| 2,306,031 A | * | 12/1942 | Anderson et al. | 5/602 |
| 3,020,909 A | * | 2/1962 | Stevens | 602/39 |
| 4,426,071 A | * | 1/1984 | Klevstad | 5/602 |
| 5,902,220 A | | 5/1999 | Lin | |
| 6,953,443 B2 | | 10/2005 | Hay | |
| 6,983,501 B2 | * | 1/2006 | Heimbrock et al. | 5/602 |
| 7,832,035 B2 | * | 11/2010 | Walczyk | 5/648 |

OTHER PUBLICATIONS

2008 Bryton Corporation Catalog, 310 Guion Rd, Indianapolis, IN 46254-3111 Entire Catalog.

* cited by examiner

*Primary Examiner* — Michael Trettel
(74) *Attorney, Agent, or Firm* — J. Curtis Edmondson (57) ABSTRACT

The present inventive subject matter is the method of use as well as a device or fixture for positioning and manipulating a patient's lower extremity for surgical and diagnostic procedures where alignment is critical and minute adjustments may be required. Once firmly attached to the operating table, the device prevents the patient's extremity from moving after the physician has selected the precise position for the elected procedure. This is achieved by a combination of a fracture reduction plate, posts, shimming blocks and an articulating and rotating frame or cradle with an adjustable and lockable rack and gear configuration and pivot joints attached to a foot assembly which acts as a leg and foot splint. The cradle is attached to the patient via a series of adjustable straps preventing the extremity from moving independently of the cradle.

8 Claims, 7 Drawing Sheets

LOWER EXTREMITY SURGICAL POSITIONING DEVICE

PRIORITY

The present inventive subject matter claims the priority of Provisional Patent Application 61/154,773, submitted Feb. 24, 2009.

BACKGROUND

The present inventive subject matter relates to a lower extremity surgical positioning device. In particular, a device or fixture that holds the leg of a patient stationary, so that medical procedures can be performed.

Traditionally surgery on the lower leg of a patient is accomplished by two individuals: the surgeon who is responsible for the actual operation procedure on the leg and the physician's assistant, who is responsible for holding and maintaining the lower leg in the proper position while surgery occurs and also for providing the retraction of tissues for optimal surgical site view for the surgeon. To improve the job of the physician assistant, a number of devices are employed to help hold the limb in position along with a variety of tissue retraction tools. These devices vary, but are typically consist of pads, buttresses, straps, and various fixtures. For example, the Bryton Corporation (Indianapolis, Ind.) markets a number of products that aid in surgery (See the 2008 Bryton Catalog, which is incorporated herein by reference).

U.S. Pat. No. 5,290,2220 (1994) issued to Guhl discloses a non-invasive distraction system for ankle arthroscopy that utilizes a sling wrapped around the patient's ankle with an adjustable tension device that provides distraction of the leg and joints because the knee is cradled in a conventional urology leg holder and held relatively stationary. The device can be mounted on a standard operating table and utilizes the bent knee and the patient's weight to aid in the distraction.

U.S. Pat. No. 6,953,443 (2005) issued to Hay discloses a tibial distraction device that is essentially a triangular ramp that functions similarly to Guhl, but is not mounted directly to the operating table.

Although these methods and devices have their uses, they have their pitfalls because they are not very precise, are prone to slippage, and are difficult to adjust.

In general there is a need for a lower extremity surgical positioning device that provides:

Access to surgical sites between the knee and foot through the positioning of the leg.
Non-invasive Distraction of fractures and/or ankle joint.
Non-invasive Compression of fractures post re-alignment.
Ability to rotate the distal aspect of the limb during distraction or compression and at the same time maintains fracture positioning.
Reduce the need for intra-operative use of external fixation traction.
Better access of intra-operative radiography.
Un-obstructed x-ray view of bones through radio-lucent material.
Precise incremental adjustments to the patient's limb.
Ease of use, such as quick mounting and dismounting onto surgical tables as well as ease of disassembly for sterilization.

It is therefore an object of the present inventive subject matter to provide a lower extremity surgical positioning device for such surgical procedures, including, but not limited to, ankle arthroscopy, tibia fractures, fibula fractures, bimaleollar/trimaleollar fractures as well as pylon fractures that is easily adjusted, capable of distraction, as well as compression, precise secured limb positioning, radiolucent, easily mounted and dismounted to the operating table and with secure positioning retention.

The present inventive subject matter also results in an overall reduction in operation time due to better surgical site access, quicker fracture reduction, faster x-ray time, and faster wound-closure through better positioning.

In summation, the inventive subject matter provides for:
Multi-planar motion for fracture reduction.
Quick lockdown of a reduction through positioning with distraction and compression settings.
Control of the varus/valgus drift after reduction.
A consistent, easy to manipulate, controlled and measured sterile non-invasive distraction and compression device.
The elimination of intra-operative external fixation traction pins and unnecessary additional surgical wounds.
A reduction of trays/equipment required on the surgical field.
Quick limb position changes for easier surgical approach.
Bilateral wound closure access for surgeon and the assistant.
Limb elevation during surgery minimizing the need for tourniquet use.
The elimination of sand bag/bump under buttock to control ankle/foot neutral position.
Minimization of concerns over lumbar spine clearance.
The elimination of concerns of low back pain complications in patients with past history of low back pain/injury/surgeries.
Better surgical site access.

SUMMARY

The present inventive subject matter overcomes problems in the prior art by providing a device or fixture for positioning a patient's lower extremity.

In various operations and medical procedures it is required that the extremity is held stationary and located and adjusted precisely. An example of this would be surgery to pin or reconstruct a shattered bone. Alignment is critical and minute adjustments may be required. Furthermore, the device must not allow the patients extremity to move once the physician has selected the precise position for each specific task within the surgical procedure.

The present invention achieves these desired results through a combination of an articulating and rotating frame or cradle attached to a foot assembly which acts as a leg and foot splint that is firmly anchored or attached to the surgical table.

The lower leg cradle is securely attached to the patient via a series of adjustable straps around the patient's thigh, shin area, ankle, and foot which not only prevents the extremity from moving independently of the cradle, but does so in a non-evasive manner to the patient's tissue and skin.

The assembly is securely affixed to the operating table's side rail via a rail mounting clamp or rail mount. The rail mount is configurable to connect to an operating table rail and is rotatable in three degrees of freedom along the plane of the operating table.

Once the patient's extremity is securely attached to the lower leg cradle and foot assembly via the straps the physician can manipulate the extremity in a number of ways due to a rack and gear configuration and a myriad of adjustable pivot points positioned in the foot assembly, along and within the leg cradle to either lengthen or rotate various portions of the extremity against each other to distract, align, and compress the extremity such as in setting a broken bone in the leg for example.

Each of these adjustable pivot points and rack and gear components has a means of locking them in a stationary position either by a friction means or by a spring and pawl mechanism. This aids in the precise adjustment of the extremity by allowing for incremental rotation, extension, or contraction of the effected limb while also preventing slippage or misalignment of the bones or tissue.

The inventive subject matter also provides for a method of positioning a lower leg and foot for surgery that places a leg and a foot into a the lower leg cradle body, adjusting the lower leg cradle body for optimal positioning for surgery. This positioning requires adjusting a lower leg support arm that has two opposing ends, and is telescopically retractable and extendable. The lower leg support arm is attached to the rail of a conventional operating table, allowing for adjustment as well as support of the lower leg in three degrees of freedom along the calf and three degrees of freedom along the axis of the rail mount.

Succinctly, the present device allows for a means to place opposing pressure points, elevation, and downward pressure to realign and maintain alignment at a fracture site, through the use of radiolucent reduction plate, lateral and medial adjusting posts, elevating shimming blocks, and downward pressure straps.

These and other embodiments are described in more detail in the following detailed descriptions and the figures. The foregoing is not intended to be an exhaustive list of embodiments and features of the present inventive subject matter. Persons skilled in the art are capable of appreciating other embodiments and features from the following detailed description in conjunction with the drawings.

LIST OF REFERENCE CHARACTERS

100 Positioning Device
110 Rail Mount Clamp
115 Operating Table Rail
120 Lower Leg Support Arm Vertical Extending Member
125 Lower Leg Support Arm
130 Lower Leg/Calf Cradle Support Base
135 Lower Leg/Calf Cradle Body
137 Cradle Body Top Cover Plate
140 Foot Support Arm
145 Cradle Support Arm (connection between the vertical extending member and leg cradle support base)
150 Foot Plate
155 Foot/Ankle Strap
160 Leg Strap
165 Vertical Extending Member Pivot Adjuster
170 Cradle Pivot Mount
172 Lower Leg
174 Foot
190210 Foot Plate Pivot Mount
240 Gear Drive

DETAILED DESCRIPTION

Representative embodiments according to the inventive subject matter are shown in FIGS. 1-7, wherein similar features share common reference numerals. The inventive subject matter of a multi-purpose positioning device has the following method of operation.

Figure 1:
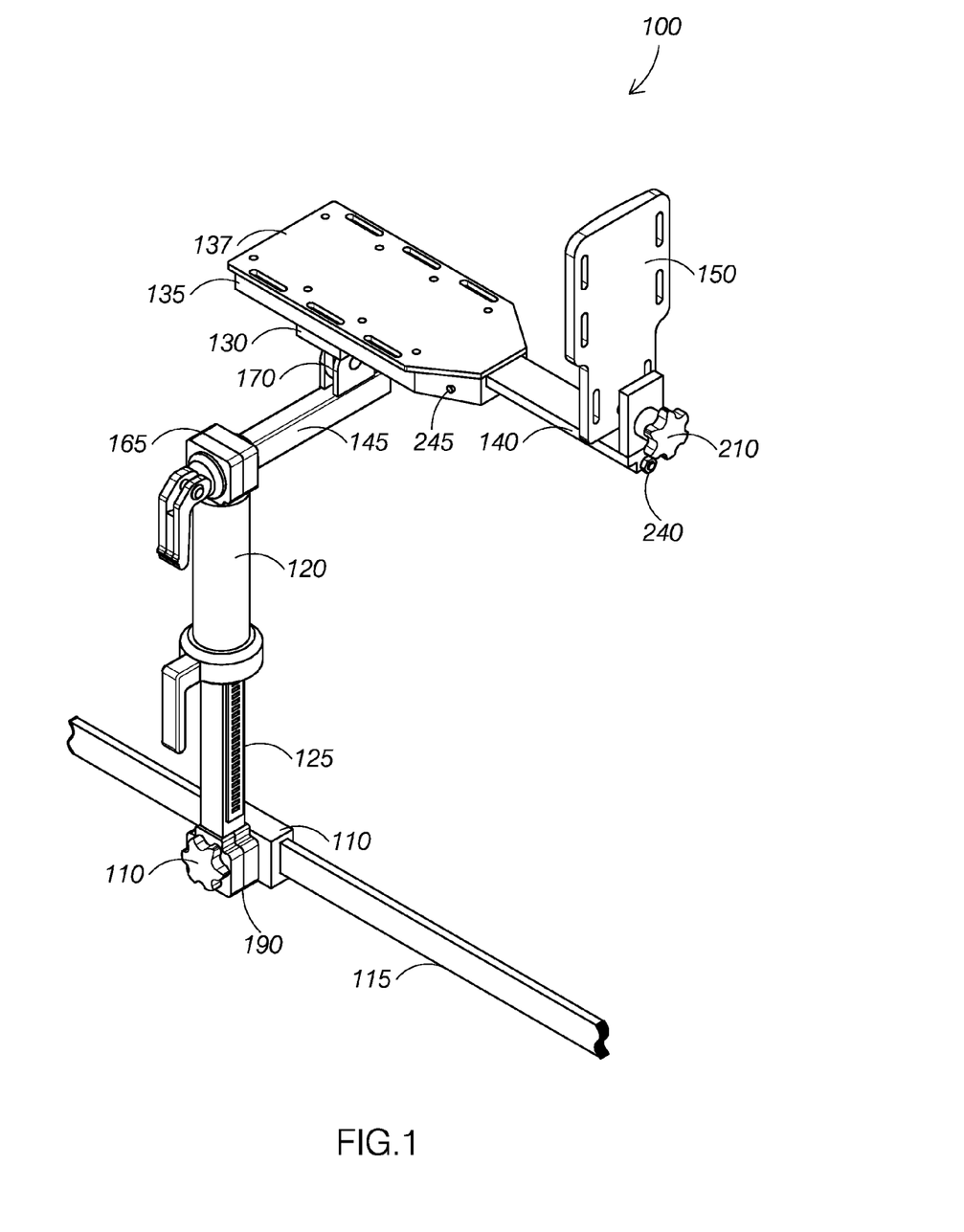
FIG. 1 is side view of Lower Extremity Surgical Positioning Device.

FIG. 1 shows a right side view of the Lower Extremity Surgical Positioning Device 100 (hereinafter "positioning device") which shows a surgical rail mount clamp 110, a lower leg support arm 125, a vertical extending member 120, and a cradle support arm, connected between a surgical rail mount clamp 110 and a leg cradle support base 130. The leg cradle body 135 is connected to the leg lower leg cradle support base 130. A foot support arm 140 connects the leg cradle body 135 to the foot plate 150. The foot plate 150 is interconnected to the foot plate pivot mount 210 which is mounted to the foot support arm 140. A foot (not shown) may be freely placed on the foot plate 150 or affixed by angle or foot straps 155.

The foot support arm 140 can be extended away from the lower leg cradle body 135 to accommodate different sized patients. The mechanism for extending the length of the foot support arm 140 may consist of any number of extension/locking mechanisms that are well known in the arts, including, but not limited to, pressure screws against internal rails, linear actuators, gear drives (240), and/or motor either stepper type, pneumatic or hydraulic.

The positioning device allows for the manipulation of the patients lower leg in at least three degrees of freedom relative to the operating table. Utilizing Cartesian coordinates will further clarify the device 100. The rail mount clamp 110 may be mounted at any point on the operating table rail 115 and would correspond to the "X" axis, running the length of a patient from head to toe, where in the "Y" axis would extend perpendicularly and upwards from then table rail 115 towards the ceiling, and the "Z" axis would be perpendicular to operating table rail 115 and parallel to the operating table surface or the operating room floor. The lower leg support arm 125 may be adjusted in relationship to the vertical extending member 120 in a telescoping fashion to adjust the height or to vary the location of the lower leg cradle body 135 in the "Y" plane to allow for better access by the surgeon. Also, in one embodiment, the lower leg support arm 125 is pivotally connected to the rail mount clamp 110 with a friction lock or lower leg pivot adjuster 190. Also, the lower leg support arm vertical extending member is pivotally connected to the cradle support arm 145 with a friction lock or pivot adjuster 165. These three adjustment points provide a flexible means of adjusting the leg in the operating table x-y-z frame of reference.

Figure 2:
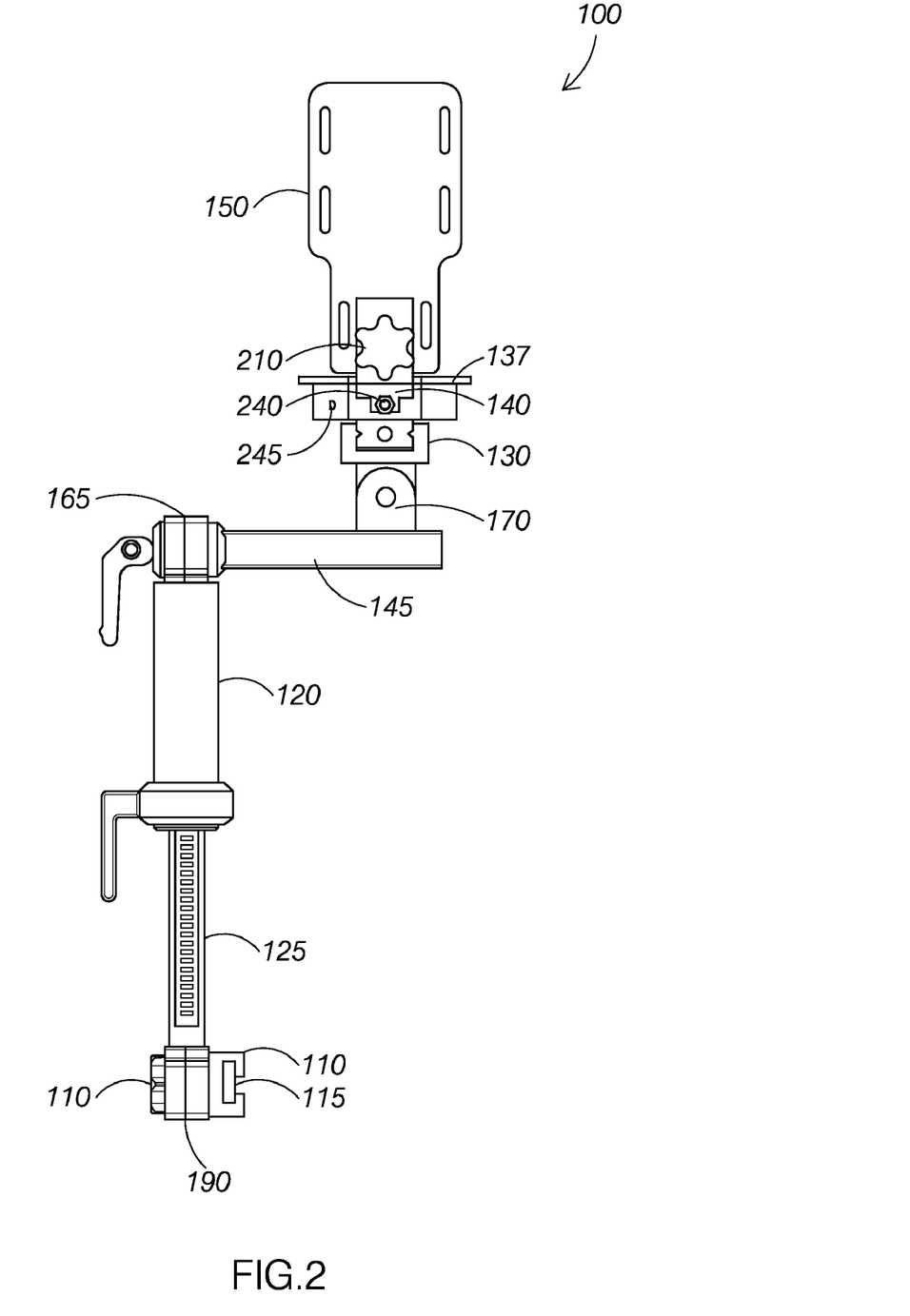
FIG. 2 is a rear view of the Lower Extremity Surgical Positioning Device.

Now referring to FIG. 2, is a rear view of the positioning device 100. As shown in FIG. 2, the rail mount clamp 110 is affixed to the operating table rail (not shown) and pivotally connected to the vertical extending member 125, which is in turn connected to the lower leg support arm 120. The support arm 120 is attached to the lower leg cradle support base 130 that is connected to the lower leg cradle body 135. The foot support arm 140 is inserted into the leg cradle body 135 at one end and terminates at the other end into a ball joint or foot plate pivot mount 210 (as seen in FIG. 1) that is attached to the foot plate 150 wherein the heal and sole of the patient's foot (not shown but depicted in FIG. 4) are positioned or rest against. The interface between the lower leg cradle body 135 and the foot support arm 140 allow for the traction and distraction of the lower leg along the "X" axis, while the pivot mount 210 allows the ankle and foot to be rotated along the "X", "Y" and "Z" axis or in line with the ankle joint. The interface between the lower leg cradle support base 130 and the pivot mount 170 allows the entire leg to be rotated along the "Z" axis.

The foot plate 150 may have alternative embodiments such as a built in buckle clip as well as the cradle pivot mount 210 which has been contemplated in various embodiments as either, a ball joint for multi-directional pivoting, a ball joint with quick release and lock handle, and a ball joint secured on a leg extrusion plate. One embodiment of the foot plate 150 contemplates an extrusion plate with grooves on the plate.

Figure 3:
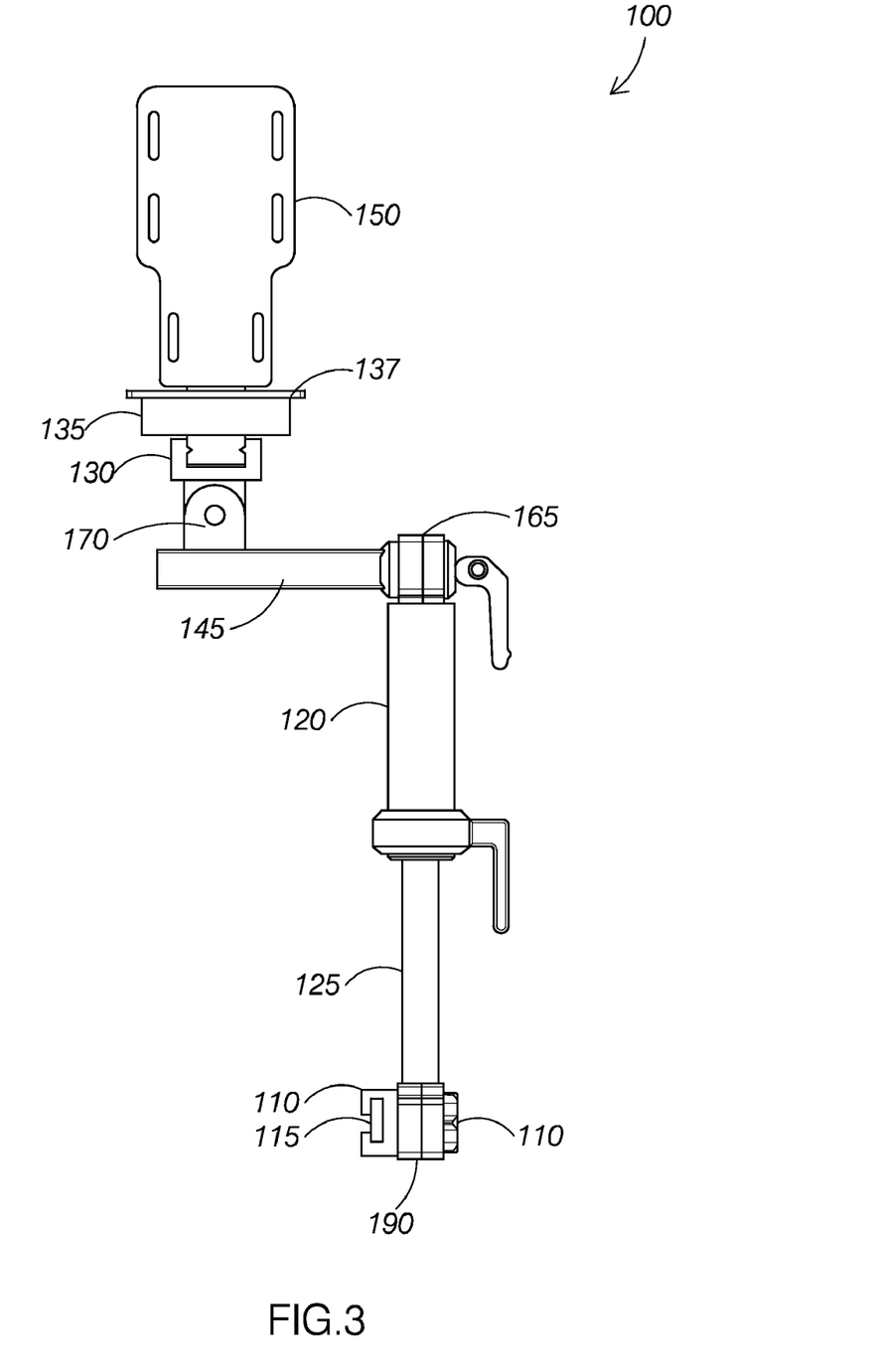
FIG. 3 is a front view of the Lower Extremity Surgical Positioning Device.

Now referring to FIG. 3 which, is a rear view of the positioning device 100. As shown in FIG. 2, the rail mount clamp 110 is affixed to the operating table rail (not shown) and pivotally connected to the lower leg support arm 120, which is in turn connected to the cradle support arm 145 through the vertical extending member pivot adjuster 165. The cradle support arm 145 is attached to the lower leg cradle support base 130 through the cradle pivot mount 170. The interface between the lower leg cradle support base 130 and the pivot mount 170 allows the entire leg to be rotated along the "Y" axis. The cradle support base 130 may be mounted at any point on the lower leg cradle body 135 and would correspond to the "X" axis allowing further limb positioning adjustments. The foot support arm 140 is inserted into the leg cradle body 135 at one end and terminates at the other end into a ball joint or foot plate pivot mount 210 (as seen in FIG. 1) that is attached to the foot plate 150 wherein the heal and sole of the patient's foot (not shown but depicted in FIG. 4) are positioned or rest against.

The interface between the lower leg cradle body 135 and the foot support arm 140 allow for the traction and distraction of the lower leg along the "X" axis, while the pivot mount 170 allows the entire leg to be rotated along the "Z" axis or in line with the ankle joint.

Figure 4:
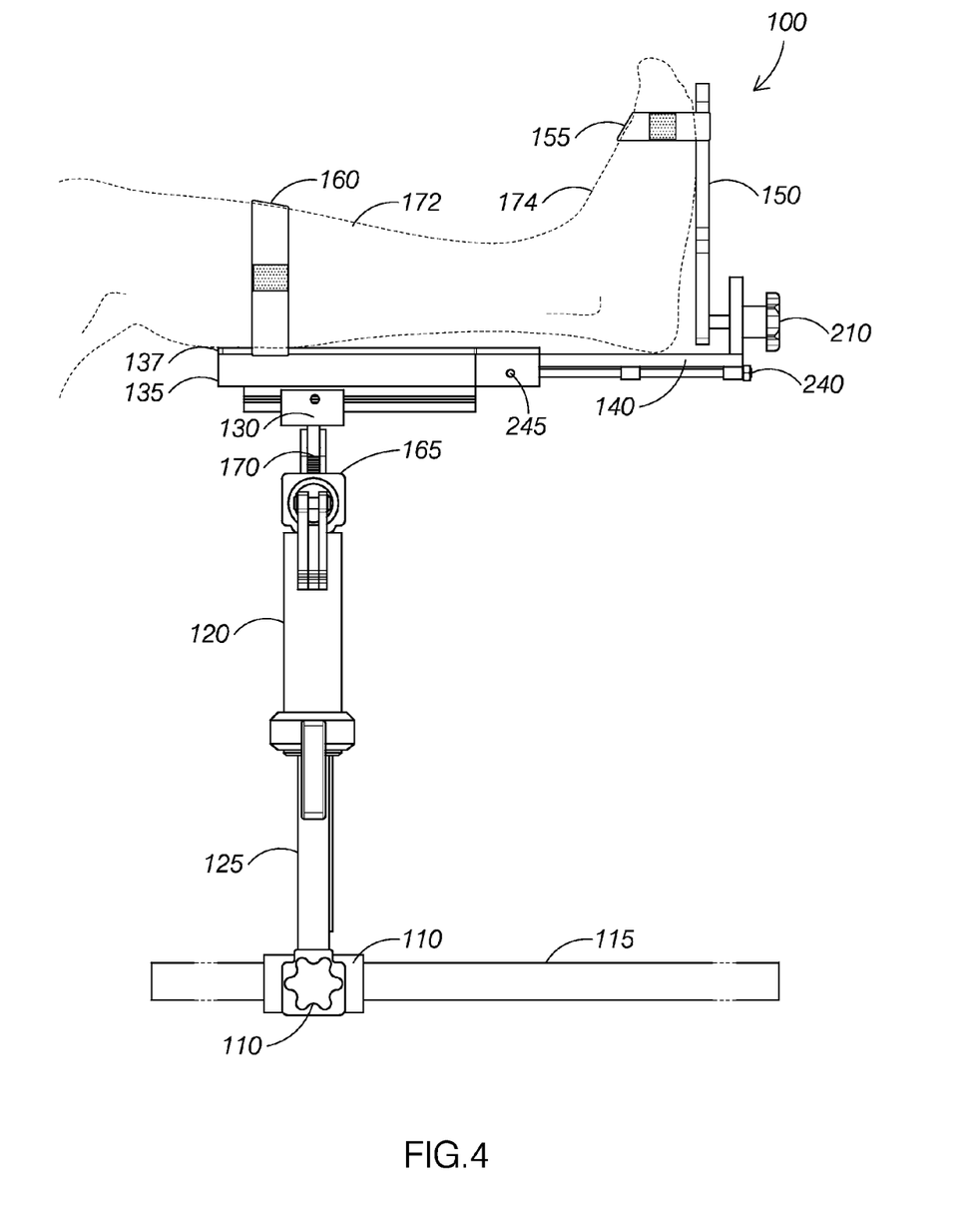
FIG. 4 is a side view of the Lower Extremity Surgical Positioning Device with an illustration of the foot and leg.

Now referring to FIG. 4 is a side view of the Lower Extremity Surgical Positioning Device with an illustration of the leg 172 and foot 174 inserted into the positioning device 100. The positioning device 100 is also shown mounted to the operating table's railing and adjustment along the "X" axis. The foot and ankle straps 155 hold the foot and ankle to the foot plate while the leg straps 160 hold the leg onto the lower leg cradle body 135.

Figure 5:
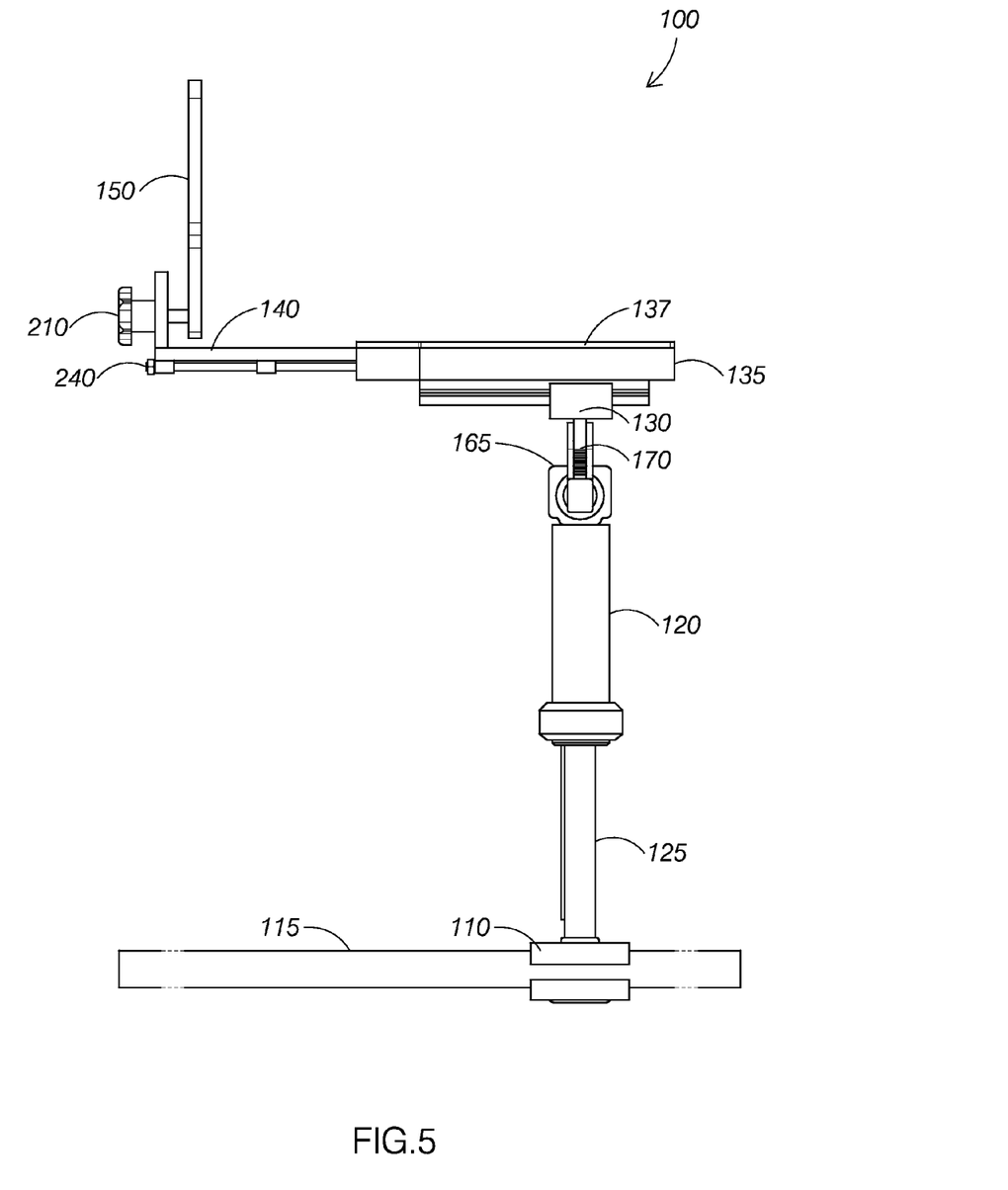
FIG. 5 is a side view of the Lower Extremity Surgical Positioning Device.

FIG. 5 is a side view of the leg cradle body 135. One embodiment of the lower leg cradle body 135 has a gear drive mechanism 240 attached to the foot support arm 140. This is actuated by a gear lock and release 245 hat may support three positions: (1) the locked position; (2) the semi-locked position, which allows for the torque wrench movement without the application of excessive tension; (3) the embodiment also allows for the complete release of the gear drive allowing free movement and remove of the foot support arm from the lower leg cradle body. The gear drive 240 may be adjusted by an Allen bit that fits the torque wrench.

Figure 6:
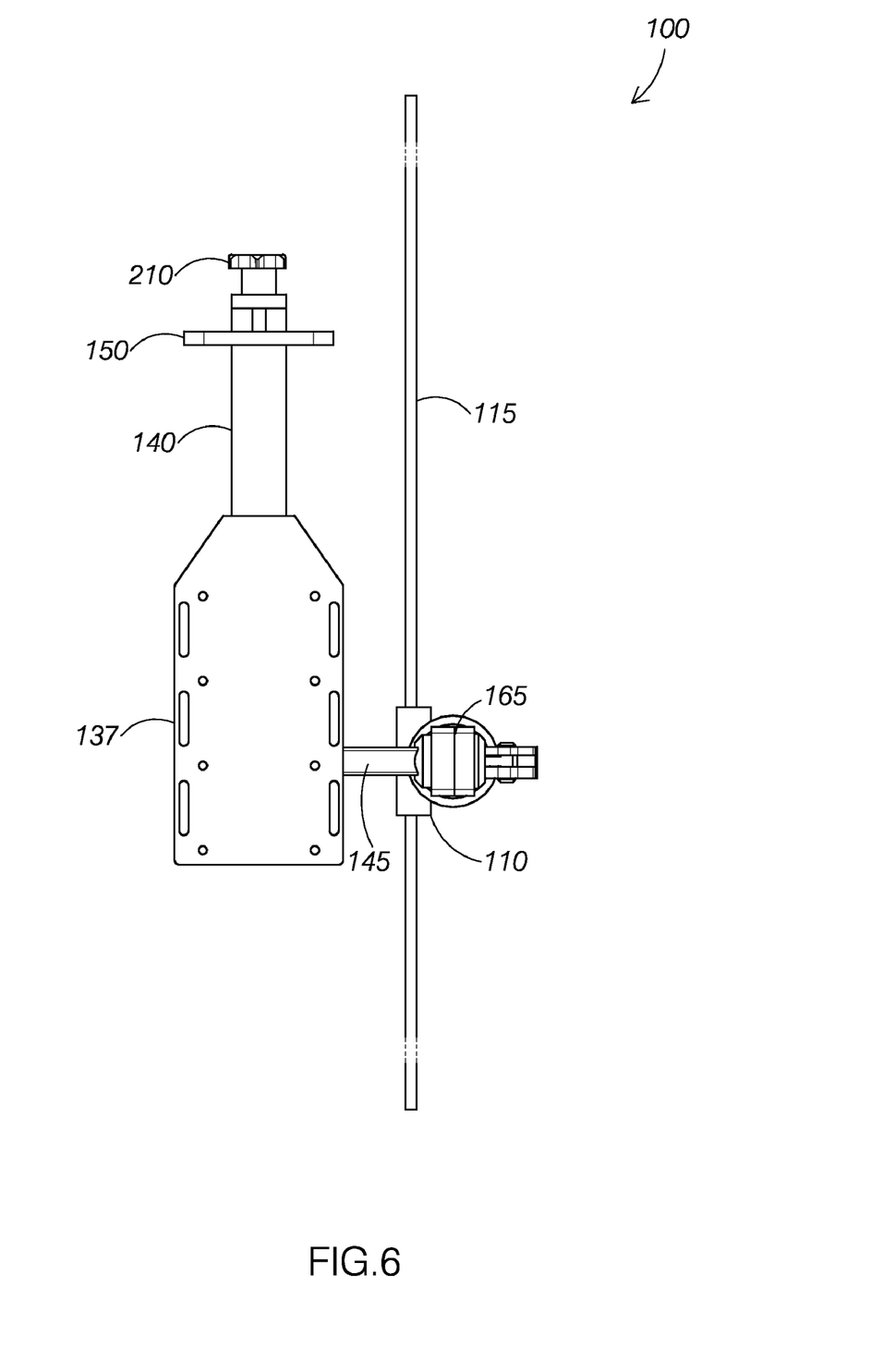
FIG. 6 is a top view of the Lower Extremity Surgical Positioning Device.

FIG. 6 is a top view of the leg cradle body. In this embodiment, the lower leg cradle body 135 has a tapered design with dimensions of about 10 cm in width and 25 cm in length. The lower leg cradle body has a top cover plate 137 with slotted gaps of 1 cm by 4 cm for straps attachments.

Figure 7:
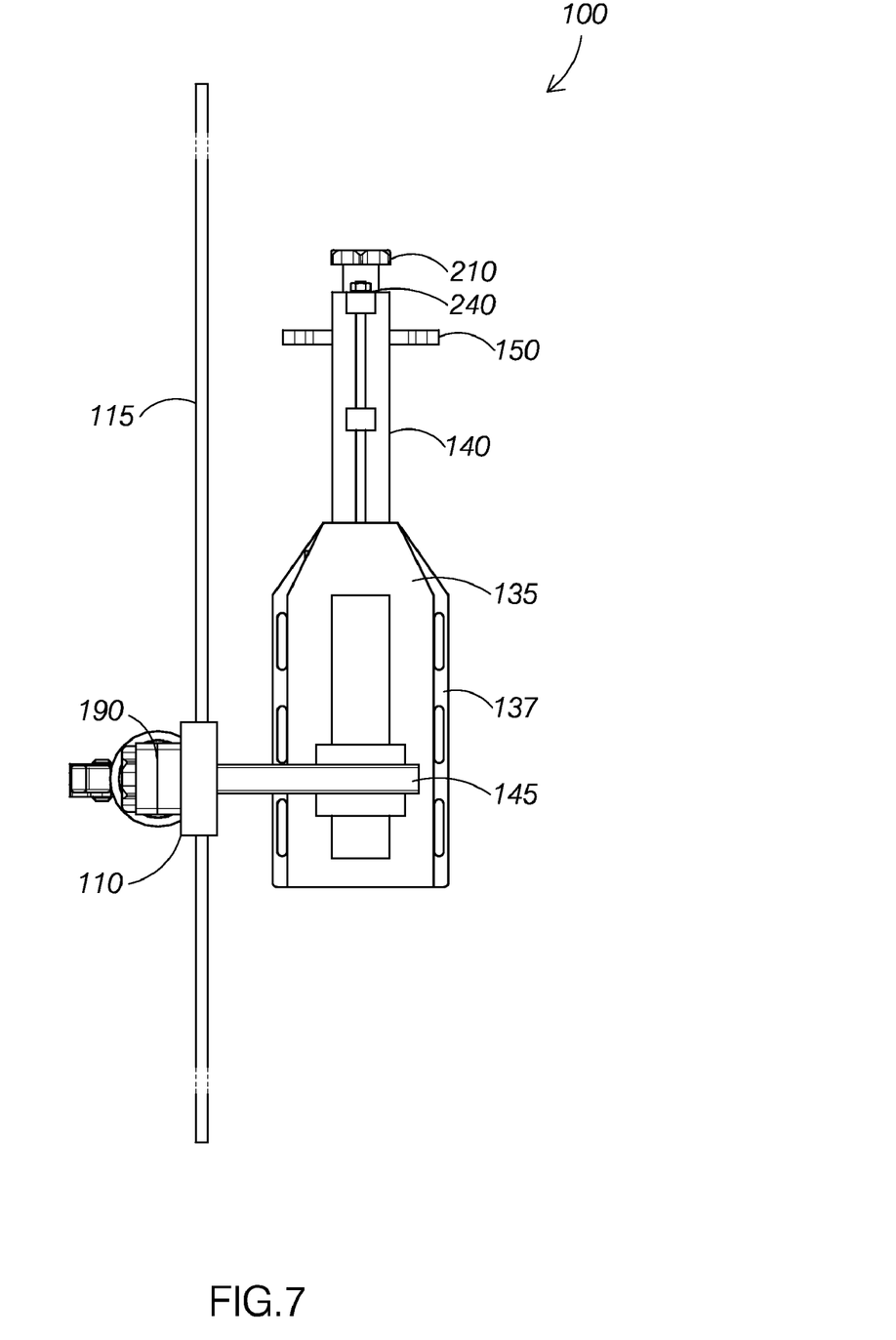
FIG. 7 is a bottom view of the Lower Extremity Surgical Positioning Device.

FIG. 7 is a bottom view of the leg cradle body. The bottom view illustrates the rail mount clamp 110 that can be affixed to the operating table and allow the entire apparatus to be moved parallel to the bedside.

The leg cradle support base 130 has three alternate embodiments. In one embodiment, the shaft of the lower leg cradle support base 130 is approximately 10 cm in length. The shaft is approximately 2.5 cm in diameter. The height of the assembly is approximately 7.5 cm. The adjustment of the mount can be accomplished by slotted indexing grooves 165 in 10 degree increments. Alternate embodiments would utilize and electronic motor positioning elements.

In alternate embodiments of the straps 160 for the upper leg and lower leg cradle body. An implementation of the support straps for the upper and lower leg has a pliable material with a foam backing. The overall dimensions are 10 cm in width and 50 cm in length, with 30 cm as a strap.

Also in another embodiment of the straps, an ankle strap is used that encompasses the foot and ankle to prevent unwarranted motion. To prevent movement, the foot and ankle strap has a ring design where the rings are about 2 cm in diameter.

The configuration of the aforementioned inventive subject matter should not be limited to any single embodiment described; instead all possible configurations that can be implemented and derived by one skilled in the arts are understood to be embodied herein.

Method and Operation of the Inventive Subject Matter

The inventive subject matter of a multi-purpose positioning device has the following method of operation.

The methodology used will vary from physician to physician as well as from procedure to procedure, as well as the order of adjustment may vary. It is also noted that standard operating procedures will be use, but not discussed herein, such as the use of gauze and sterile environment practices.

The general use of the device 100 requires that the patient is placed or laid prone on the operating table. As shown on FIG. 4, the patient's lower leg and foot is placed into the positioning device 100. The lower leg cradle support base 130 is placed such that the lower leg 172 and the foot 174 are securely mounted on the lower leg cradle body 135 and the foot support arm 140 by the use of foot straps 155 and leg straps 160.

The lower leg cradle body 135 and the foot support arm 140 are adjusted to provide for specific patient limb length by extending or retracting the foot support arm 140 relative to the lower leg cradle body 140. One embodiment has a bifurcation in the lower leg cradle body 135 wherein the foot support arm 140 is part of the lower leg cradle body 135 and is so interleaved, so that the overall length of the lower leg cradle body 135 may be extended or reduced in length to accommodate varied leg sizes.

Adjustment of the height of patient's lower leg 172 is achieved by raising and lowering the lower leg cradle body 135 by moving the vertical extending member 120 towards or away from the lower leg support arm 125. In one embodiment of the inventive subject matter, the support arm 125 and vertical extending member 120 consists of a telescopically retractable and extendable hollow tubular pole sections allowing the length to be adjusted manually. In another embodiment, the support arm 125 and vertical extending member 120 is extended and/or retracted using an electronic or hydraulics means, such as a linear actuator or piston configuration, thereby manipulating the lower leg cradle body 135 in the "Y" frame of reference.

The patient's lower leg can be further adjusted as needed by rotating the lower leg support arm 125 which is pivotally connected to the operating rail 115 through the rail mount clamp 110 and then locked in position by the lower leg pivot adjuster 190 which allows the support arm to rotate approximately 180 degrees around the "Y" frame of reference. In one embodiment of the inventive subject matter, the adjuster pivot is manually adjusted, but other embodiments would allow for electrical or hydraulics adjustments.

Further adjustments can be made at lower leg cradle support base 130 which will cause the lower leg cradle body 135 and the patient's lower leg 172 to rotate along the "X" axis. The foot plate 150 is connected to a cradle pivot allowing for manipulation of the patient's foot 174 along the "Z" and "Y" plans.

It has been contemplated in various embodiments to use a variety of position locking configurations, to ensure that once an adjustment has been made, there will be no further movement. These locking configurations include, but are not limited to simple friction locking structures, such as a knob and screw, gear and pawls, and combinations of springs and spring materials.

The materials as depicted in FIG. 1 can be fabricated from materials generally used in operating room environments. These materials may be also constructed from metal, plastic, or carbon fiber products. The use of wood laminates and/or wood can be utilized. In operating environments where X-Rays will need to be taken while the leg is inserted into the positioning device 100, the material should be fabricated from radio-lucent material.

Persons skilled in the art will recognize that many modifications and variations are possible in the details, materials, and arrangements of the parts and actions which have been described and illustrated in order to explain the nature of this inventive concept and that such modifications and variations do not depart from the spirit and scope of the teachings and claims contained therein.

All patent and non-patent literature cited herein is hereby incorporated by references in its entirety for all purposes.

I claim:

1. A lower extremity surgical positioning device comprising:
   a rail mount clamp being configurable to be positioned and capable of receiving an operating table rail;
   a lower leg support arm extending vertically upwards from the rail mount clamp with a first and a second end pivotally affixed to the rail mount clamp at the first end;
   a vertical extending member with a first and second end with the first end attached to the lower leg support arm's second end allowing the distance between the rail mount clamp and the lower leg support arm to vary in distance;
   a lower leg cradle support base affixed to the second end of the vertical extending member;
   a lower leg cradle body pivotally affixed to the lower leg cradle support base allowing for incremental rotational adjustment and fixation along the direction of the operating table rail.

2. The lower extremity surgical positioning device as in claim 1 further comprising:
   a foot support arm with a first and a second end; the first end of the foot support arm further comprising: an interleaved section proximate to a lower leg cradle support, the lower leg cradle support allowing for extension or retraction of the combined overall length of the foot support arm and the lower leg cradle support;
   a foot plate;
   and a cradle pivot connecting the second end of the foot support arm to the foot plate with a means of rendering the pivot stationary.

3. The lower extremity surgical positioning device as in claim 1 further comprising:
   a bifurcation in the lower leg cradle body, the bifurcation having a lower leg body and a foot support arm,
   wherein the foot support arm is interleaved in the lower leg cradle body so that a calf cradle mount may be extended or reduced in length.

4. The lower extremity surgical positioning device as in claim 1 further comprising:
   a foot support arm fabricated from radio lucent materials.

5. The lower extremity surgical positioning device as in claim 1 further comprising:
   a foot strap, wherein said foot strap is connected to a foot plate, such that the foot strap is capable of receiving a foot.

6. The lower extremity surgical positioning device as in claim 1 further comprising:
   a leg strap, wherein the leg strap is connected to a cradle body top cover plate,
   such that the cradle body top cover plate is capable of receiving a leg.

7. The lower extremity surgical positioning device as in claim 1 further comprising:
   a means for preventing rotation and rendering stationary a multiplicity of securing screws.

8. The lower extremity surgical positioning device as in claim 1 further comprising:
   the vertical extending member having a means for preventing rotation of the vertical extending member.

* * * * *